(12) United States Patent
Perry et al.

(10) Patent No.: US 9,173,397 B2
(45) Date of Patent: Nov. 3, 2015

(54) FORMULATION COMPONENT

(75) Inventors: Richard Brian Perry, Bracknell (GB); Ian David Perry, legal representative, Bracknell (GB); Gordon Alastair Bell, Bracknell (GB); Phillip Taylor, Bracknell (GB); Julia Lynne Ramsay, Bracknell (GB); David Stock, Bracknell (GB)

(73) Assignee: Syngenta Limited, Surrey (GB)

( * ) Notice: Subject to any disclaimer, the term of this patent is extended or adjusted under 35 U.S.C. 154(b) by 55 days.

(21) Appl. No.: 14/113,456

(22) PCT Filed: Apr. 26, 2012

(86) PCT No.: PCT/GB2012/000340
§ 371 (c)(1),
(2), (4) Date: Jan. 6, 2014

(87) PCT Pub. No.: WO2012/146888
PCT Pub. Date: Nov. 1, 2012

(65) Prior Publication Data
US 2014/0148342 A1 May 29, 2014

(30) Foreign Application Priority Data
Apr. 26, 2011 (GB) .................................. 1107040.6

(51) Int. Cl.
*A01N 25/00* (2006.01)
*A01N 43/54* (2006.01)
*A01N 25/30* (2006.01)
*A01N 25/02* (2006.01)
*A01N 37/10* (2006.01)

(52) U.S. Cl.
CPC ................ *A01N 43/54* (2013.01); *A01N 25/02* (2013.01); *A01N 25/30* (2013.01); *A01N 37/10* (2013.01)

(58) Field of Classification Search
CPC ............................... A01N 31/02; A01N 25/30
USPC ......................................................... 504/358
See application file for complete search history.

(56) References Cited

U.S. PATENT DOCUMENTS

| 5,698,210 A | 12/1997 | Levy | |
|---|---|---|---|
| 2003/0069135 A1* | 4/2003 | Kober et al. | ................ 504/116.1 |
| 2006/0173142 A1* | 8/2006 | Nava et al. | .................... 525/540 |

FOREIGN PATENT DOCUMENTS

| EP | 1344454 | | 9/2003 | |
|---|---|---|---|---|
| GB | 2002635 | | 2/1979 | |
| GB | 2306327 A | * | 5/1997 | ............. A01N 25/30 |
| JP | WO9517817 | | 7/1995 | |

OTHER PUBLICATIONS

International Search Report for International Patent Application No. PCT/GB2012/000340 dated Oct. 1, 2012.

* cited by examiner

*Primary Examiner* — Johann R Richter
*Assistant Examiner* — Danielle Sullivan
(74) *Attorney, Agent, or Firm* — James Cueva

(57) ABSTRACT

The invention relates to the use of aromatic esters as adjuvants in compositions, particularly for agrochemical use, as well to compositions comprising such an aromatic ester, in combination with at least one agrochemical and at least one surfactant. The invention further extends to methods of making and using such compositions. In particular the present invention relates to such compositions when formulated as, or comprised by, an emulsion concentrate (EC), an emulsion in water (EW), a suspension of particles in water (SC), a microcapsule formulation (CS), a suspension of particles in the continuous phase of an emulsion (SE), a dispersion concentrate (DC) or an oil suspension (OD).

12 Claims, No Drawings

FORMULATION COMPONENT

RELATED APPLICATION INFORMATION

This application claims priority under 35 U.S.C. § 371 from PCT Application No. PCT/GB2012/000340, filed 13 Apr. 2012, which claims the benefit of European Patent Application 1107040.6, filed 26 Apr. 2011, the disclosures of which are incorporated by reference herein.

This invention relates to the use of aromatic esters as adjuvants in compositions, particularly for agrochemical use, as well to compositions comprising such an aromatic ester, in combination with at least one agrochemical and at least one surfactant. The invention further extends to methods of making and using such compositions. In particular the present invention relates to such compositions when formulated as, or comprised by, an emulsion concentrate (EC), an emulsion in water (EW), a suspension of particles in water (SC), a microcapsule formulation (CS), a suspension of particles in the continuous phase of an emulsion (SE), a dispersion concentrate (DC) or an oil suspension (OD).

The efficacy of the active ingredients (AIs) in an agrochemical composition can often be improved by the addition of further ingredients. The observed efficacy of the combination of ingredients can sometimes be significantly higher than that which would be expected from the individual ingredients used (synergism). An adjuvant is a substance which can increase the biological activity of and AI but is itself not significantly biologically active. The adjuvant is often a surfactant, and can be included in the formulation or added separately, e.g. by being built into emulsion concentrate formulations, or as tank mix additives.

In addition to the effect on biological activity, the physical properties of an adjuvant are of key importance and must be selected with a view to compatibility with the formulation concerned. For instance, it is generally simpler to incorporate a solid adjuvant into a solid formulation such as a water-soluble or water-dispersible granule. In general adjuvants rely on surfactant properties for biological activity enhancement and one typical class of adjuvants involves an alkyl or aryl group to provide a lipophilic moiety and a (poly)ethoxy chain to provide a hydrophilic moiety. Much has been published on the selection of adjuvants for various purposes, such as Hess, F. D. and Foy, C. L., Weed technology 2000, 14, 807-813.

The present invention is based on the discovery that aromatic esters with relatively long hydrocarbon chains are surprisingly effective adjuvants, significantly enhancing the biological activity of active ingredients. Aromatic esters of varied hydrocarbon chain lengths have until now only been known as solvents (such as Benzoflex 181™ and Finsolv TN™), emollients, plasticisers, and thickening agents, for use in various industries. There is also a meagre amount of information presently available on preferentially shorter chain aromatic esters having putative adjuvant properties in the context of agrochemical compositions. However, according to the present invention, it is in fact longer chain aromatic esters (in particular trimellitate derivatives) which possess the greater adjuvant properties.

The present invention accordingly provides an agrochemical composition comprising:
i. an active ingredient
ii. a surfactant
iii. an aromatic ester of formula (I)

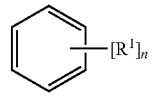

wherein
$R^1$ is $COOR^2$
n is an integer selected from 3, 4, 5 and 6; and
each $R^2$ is independently selected from the group consisting of $C_4$-$C_{20}$ alkyl, $C_4$-$C_{22}$ alkenyl, $C_4$-$C_{22}$ alkyldienyl and $C_6$-$C_{22}$ alkyltrienyl.

In a second aspect the invention provides for the use of an aromatic ester of formula (I) as described herein as an adjuvant in an agrochemical composition.

In a third aspect the invention provides for the use of an agrochemical composition as described herein to control pests.

In a further aspect there is provided a method of controlling a pest, comprising applying a composition of the invention to said pest or to the locus of said pest.

In yet a further aspect there is provided a method of making an agrochemical composition as described herein, comprising combining an active ingredient, a surfactant and an aromatic ester of formula (I).

Alkyl groups and moieties are straight or branched chains, and unless explicitly stated to the contrary, are unsubstituted. Examples of suitable alkyl groups for use in the invention are hexyl, heptyl, octyl, nonyl, decyl, undecyl, dodecyl, tridecyl, tetradecyl, pentadecyl, hexadecyl, heptadecyl, octadecyl, nonadecyl and eicosyl groups.

Alkenyl groups and moieties are straight or branched chains having a single carbon-carbon double bond, and unless explicitly stated to the contrary, are unsubstituted. Examples of suitable alkenyl groups for use in the invention are hex-1-enyl, hex-2-enyl, hex-3-enyl, hept-1-enyl, oct-1-enyl, non-1-enyl, dec-1-enyl, undec-1-enyl, and groups derived from monoenoic fatty acids including cis-4-decenyl, cis-9-decenyl, cis-5-laurolyl, cis-4-dodecenyl, cis-9-tetradecenyl, cis-5-tetradecenyl, cis-4-tetradecenyl, cis-9-hexadecenyl, cis-6-hexadecenyl, cis-6-octadecenyl, cis-9-octadecenyl, trans-9-octadecenyl, cis-11-octadecenyl, cis-9-eicosenyl, cis-11-eicosenyl, cis-11-docosenyl, cis-13-docosenyl and cis-15-tetracosenyl.

Alkyldienyl groups and moieties are straight or branched chains having two carbon-carbon double bond, and unless explicitly stated to the contrary, are unsubstituted. Examples of suitable alkyldienyl groups for use in the invention are buta-1,3-dienyl, penta-1,3-dienyl, penta-2,4-dienyl, penta-1,4-dienyl, hex-1,3-dienyl, hept-1,3-dienyl, linoleyl and linoelaidyl.

Alkyltrienyl groups and moieties are straight or branched chains having three carbon-carbon double bond, and unless explicitly stated to the contrary, are unsubstituted. Examples of suitable alkyldienyl groups for use in the invention hex-1,3,5-trienyl, hepta-1,3,5-trienyl and linolenyl.

In particularly preferred embodiments of the invention, the preferred values for n, as well as the preferred groups for $R^1$ & $R^2$, in any combination thereof (unless specifically stated otherwise) are as set out below.

As described herein, compounds of formula (I) may be esters of hemimellitic, trimelitic, trimesic, mellophanic, prehnitic, pyromellitic, benzene-pentacarboxylic and mellitic acids. Preferably, each $R^2$ is independently a $C_4$-$C_{20}$ alkyl group. More preferably each $R^2$ is independently a $C_6$-$C_{20}$ alkyl group, more preferably a $C_6$-$C_{13}$ alkyl group and may be for example n-hexyl, isoheptyl, 2-ethylhexyl, isononyl, isodecyl, isoundecyl, isododecyl, or isotridecyl. Most preferably each $R^2$ is a $C_6$-$C_{10}$ alkyl group.

In certain embodiments each $R^2$ is independently a $C_6$, $C_8$ or $C_{10}$ alkyl group. In further embodiments each $R^2$ is independently n-hexyl, 2ethylhexyl or isodecyl.

As described herein n may be an integer selected from 3, 4, 5 or 6, preferably 3. In particularly preferred embodiments when n is 3, each $R^2$ is the same.

Examples of compounds of formula (I), which may be used in the invention and which are available commercially include for example, those described in Table 1 below.

TABLE 1

Compounds of formula (I) for use in the invention

| Compound | Trade name | Supplier | CAS no. |
|---|---|---|---|
| Tri-n-hexyl trimellitate | MORFLEX ® 560 | Vertellus | 1528-49-0 |
| Tris-2-ethylhexyl trimellitate | PALATINOL ® TOTM | BASF | 3319-31-1 |
| Tri-isodecyl trimellitate | MORFLEX ® 530 | Vertellus | 36631-30-08 |
| A trimellitate ester of mixed semi-linear $C_7$ and $C_9$ alcohols | DIOLUBE 1070 | Diolube | 68515-60-6 |
| A trimellitate ester of mixed semi-linear $C_8$ and $C_{10}$ alcohols | DIOLUBE 1090 | Diolube | 67989-23-5 |

Alternatively, compounds of formula 1 may be synthesised according to the general principals outlined below.

Where n has a value of 3, compounds of formula (I) are for example trimellitic acid esters and may be synthesised using well-known methodology as described for example in reaction schemes 1 and 2 below.

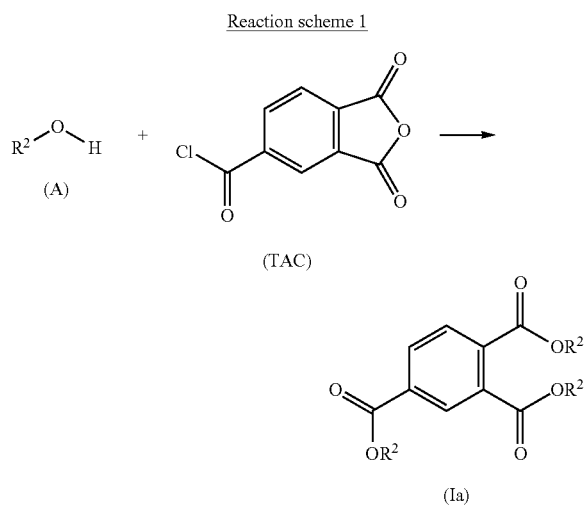

An alcohol of formula (A) is reacted with trimellitic anhydride chloride (TAC) in order to form a trimellitic acid ester of formula (Ia), wherein $R^2$ is an appropriate alkyl group as defined hereinbefore.

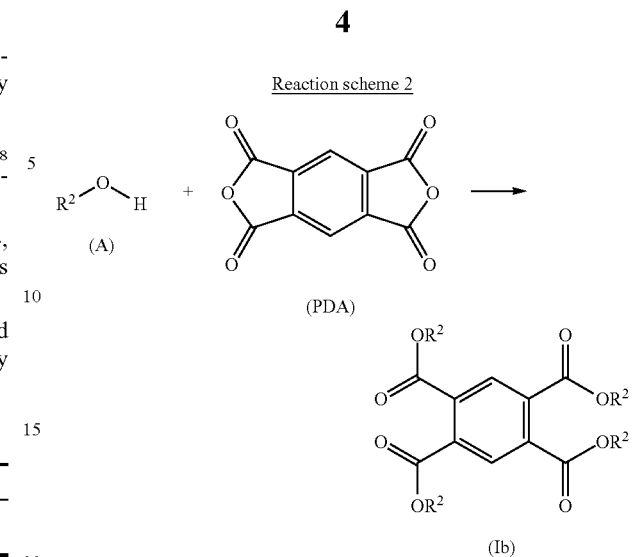

An alcohol of formula (A) is reacted with pyromellitic dianhydride (PDA) in order to form a pyromellitic acid ester of formula (Ib), wherein $R^2$ is an appropriate alkyl group as defined hereinbefore.

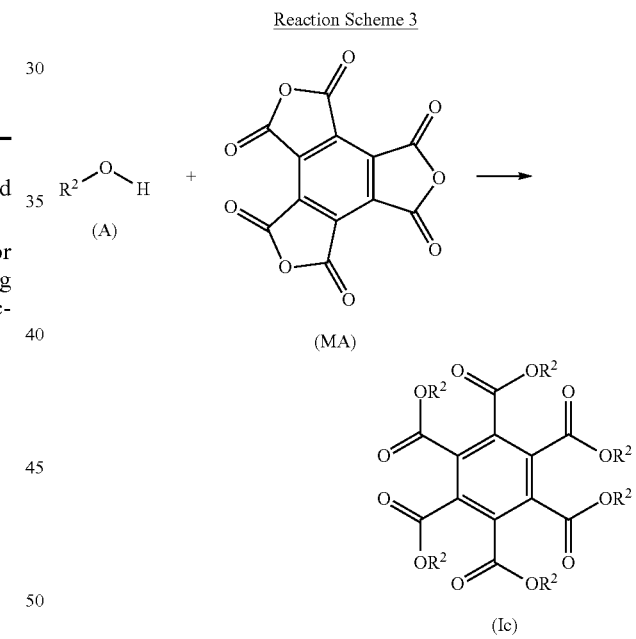

An alcohol of formula (A) is reacted with mellitic anhydride (MA) in order to form a mellitic acid ester of formula (Ic), wherein $R^2$ is an appropriate alkyl group as defined hereinbefore.

Alcohols of formula (A), acid chlorides and acid anhydrides are readily available or may be synthesised using standard methodology well known in the art.

As stated previously, the present invention is based on the unexpected finding that compounds of formula (I) are particularly good adjuvants in agrochemical formulations. Accordingly, such adjuvants may be combined with an active ingredient, which is an agrochemical, in order to form an agrochemical composition. The present invention extends to a method of making such an agrochemical composition, wherein said method comprises combining a compound of formula (I) with an agrochemically active ingredient, and optionally a surfactant. The noun "agrochemical" and term "agrochemically active ingredient" are used herein interchangeably, and they include herbicides, insecticides, nematicides, molluscicides, funcgicides, plant growth regulators, and safeners. Suitable herbicides include bicyclopyrone, mesotrione, fomesafen, tralkoxydim, napropamide, amitraz, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyciodim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron and metoxuron.

Suitable fungicides include isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin and prothioconazole.

Suitable insecticides include thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin and halfenprox.

Suitable plant growth regulators include paclobutrazole and 1-methylcyclopropene.

Suitable safeners include benoxacor, cloquintocet-mexyl, cyometrinil, dichlormid, fenchlorazole-ethyl, fenclorim, flurazole, fluxofenim, mefenpyr-diethyl, MG-191, naphthalic anhydride and oxabetrinil.

Of course, the various editions of The Pesticide Manual [especially the $14^{th}$ and $15^{th}$ editions] also disclose details of agrochemicals, any one of which may suitably be used with the present invention.

The skilled man will appreciate that compositions of the invention may comprise one or more of the agrochemicals as described above.

Compositions of the invention will typically comprise the agrochemical in an amount that is recommended in the art. Generally the agrochemical will be present at a concentration of about 0.001% to 90% w/w. The skilled man will appreciate that compositions of the invention may be in the form of a ready-to-use formulation or in concentrate form suitable for further dilution by the end user, and the concentration of agrochemical and compound of formula (I) will be adjusted accordingly. In concentrated form, compositions of the invention typically comprise agrochemical at 5 to 75% w/w, more preferably 10 to 50% w/w agrochemical. Ready-to-use compositions of the invention will typically comprise from 0.0001% to 1% w/w, more preferably from 0.001% to 0.5% w/w, and more preferably still from 0.001% to 0.1% w/w agrochemical.

Typically a compound of formula (I) will comprise from about 0.0005% to about 90% w/w of the total composition. When in concentrated form, compositions of the invention typically comprise a compound of formula (I) from 1% to 80% w/w, preferably from 5% to 60% w/w and more preferably from 10% w/w to 40% w/w. Ready to use compositions of the invention typically comprise a compound of formula (I) from about 0.05% to about 1% w/w of the total composition, more preferably still from about 0.1% to about 0.5% w/w of the total composition. In specific embodiments the aromatic ester will be included at concentrations of 0.1%, 0.2%, 0.25%, 0.3%, 0.4% or 0.5% w/w of the total composition. Compounds of formula (I) may be manufactured and/or formulated separately, and in order to be used as an adjuvant these may be added to a separate agrochemical formulation at a subsequent stage, typically immediately prior to use.

The skilled man will appreciate that compositions of the invention may be in the form of a ready-to-use formulation or in concentrate form suitable for further dilution by the end user, and the concentration of agrochemical and compound of formula (I) will be adjusted accordingly. Compounds of formula (I) may be manufactured and/or formulated separately, and in order to be used as an adjuvant these may be added to a separate agrochemical formulation at a subsequent stage, typically immediately prior to use.

Compositions of the invention may be formulated in any suitable manner known to the man skilled in the art. As mentioned above, in one form a composition of the invention is a formulation concentrate which may be diluted or dispersed (typically in water) by an end-user (typically a farmer) in a spray tank prior to application.

Additional formulation components may be incorporated alongside compounds of formula (I) or compositions of the invention in such formulations. Such additional components include, for example, adjuvants, surfactants, emulsifiers, and solvents, and are well known to the man skilled in the art: standard formulation publications disclose such formulation components suitable for use with the present invention (for example, Chemistry and Technology of Agrochemical Formulations, Ed. Alan Knowles, published by Kluwer Academic Publishers, The Netherlands in 1998; and Adjuvants and Additives: 2006 Edition by Alan Knowles, Agrow Report DS256, published by Informa UK Ltd, December 2006). Further standard formulation components suitable for use with the present invention are disclosed in WO2009/130281A1 (see from page 46, line 5 to page 51, line 40).

Thus, compositions of the present invention may also comprise one or more surfactants or dispersing agents to assist the emulsification of the agrochemical on dispersion or dilution in an aqueous medium (dispersant system). The emulsification system is present primarily to assist in maintaining the emulsified agrochemical in water. Many individual emulsifiers, surfactants and mixtures thereof suitable for forming an emulsion system for an agrochemical are known to those skilled in the art and a very wide range of choices is available. Typical surfactants that may be used to form an emulsifier system include those containing ethylene oxide, propylene oxide or ethylene oxide and propylene oxide; aryl or alkylaryl sulphonates and combinations of these with either ethylene oxide or propylene oxide or both; carboxylates and combinations of these with either ethylene oxide or propylene oxide or both. Polymers and copolymers are also commonly used.

Compositions of the present invention may also include solvents, which may have a range of water solubilitites. Oils with very low water solubilities may be added to the solvent of the present invention for assorted reasons such as the provision of scent, safening, cost reduction, improvement of the emulsification properties and alteration of the solubilising power. Solvents with higher water solubility may also be added for various reasons, for instance to alter the ease with which the formulation emulsifies in water, to improve the solubility of the pesticide or of the other optional additives in the formulation, to change the viscosity of the formulation or to add a commercial benefit.

Other optional ingredients which may be added to the formulation include for example, colourants, scents and other materials which benefit a typical agrochemical formulation.

Compositions of the invention may formulated for example, as emulsion or dispersion concentrates, emulsions in water or oil, as microencapsulated formulations, aerosol sprays or fogging formulations; and these may be further formulated into granular materials or powders, for example for dry application or as water-dispersible formulations. Preferably compositions of the invention will be formulated as, or comprised by an emulsion concentrate (EC), an emulsion in water (EW), a microcapsule formulation (CS), a suspension of particles in the continuous phase of an emulsion (suspoemulsion; SE), a dispersion concentrate (DC) or an oil suspension (OD).

Compositions of the invention may be used to control pests. The term "pest" as used herein includes insects, fungi, molluscs, nematodes, and unwanted plants. Thus, in order to control a pest a composition of the invention may be applied directly to the pest, or to the locus of a pest.

Compositions of the invention also have utility in the seed treatment arena, and thus may be applied as appropriate to seeds.

The skilled man will appreciate that the preferences described above with respect to various aspects and embodiments of the invention may be combined in whatever way is deemed appropriate.

Various aspects and embodiments of the present invention will now be illustrated in more detail by way of example. It will be appreciated that modification of detail may be made without departing from the scope of the invention.

EXAMPLES

Example 1

Use of Aromatic Acid Esters as Adjuvants in Agrochemical Compositions of Isopyrazam The efficacy of the following aromatic acid esters tri-n-hexyltrimellitate (Morflex®560) and tri-isodecyl trimellitate (Morflex®530), as adjuvants in compositions comprising isopyrazam was tested and compared to the standard formulations (both EC and SC) of the fungicide, which lack this type of adjuvant.

Wheat plants were inoculated with the fungus *Septoria tritici*. Five days after inoculation the plants were sprayed with a diluted emulsion concentrate or suspension concentrate formulation of the fungicide isopyrazam at rates of 3, 10, 30 and 100 mg of the fungicide per litre of spray solution, using a laboratory track sprayer which delivered the spray at a rate of 200 liters per hectare. Spray tests were also carried out with diluted suspension concentrate additionally comprising each of the benzoate adjuvants described above. These adjuvants were added to the spray solution at a rate of 0.5% w/w, based on the quantity of spray liquor. The adjuvant oils were emulsified using a small amount of the surfactant Pluronic® PE 10500, which was present in the composition at a concentration of 0.02% v/v. The leaves of the plants were assessed visually 14 days after the spray application and the damage was expressed as the percentage of the leaf area infected. Each spray test was replicated three times across the four application rates and the modelled means of these results are shown in Table 2 below.

TABLE 2

Mean % infection of wheat plants with *S. tritici* treated with isopyrazam in the presence and absence of benzoic acid ester adjuvants. A standard Tukey HSD test was carried out to assess whether each result was statistically different from the other results and this is expressed as a letter: tests with the same letter are not statistically different ($p < 0.05$).

| Treatment | Mean % infection |
| --- | --- |
| Blank | 21.2 A |
| Standard isopyrazam SC | 11 BC |
| Standard isopyrazam SC + Turbocharge (R) | 10.7 BC |
| Standard isopyrazam SC + Tri-n-hexyltrimellitate | 10.2 BC |
| Standard isopyrazam SC + Tri-isodecyl trimellitate | 9.5 C |
| Standard isopyrazam EC | 8.8 C |

As can be seen from Table 2 the benzoates Morflex®560 (tri-n-hexyltrimellitate) and Morflex®530 (tri-isodecyltrimellitate) were as efficacious as the commercial tank mix adjuvant Turbocharge® and as efficacious as the standard suspension concentrate and standard emulsion concentrate formulations of isopyrazam.

Example 2

Use of Aromatic Esters as Adjuvants in Agrochemical Compositions of Cyproconazole The efficacy of the following aromatic acid esters, tri-n-hexyltrimellitate (Morflex®560) and tri-isodecyl trimellitate (Morflex 530), as adjuvants in compositions comprising cyproconazole was tested and compared to the standard SC formulation of the fungicide, which lacks this type of adjuvant, and to the SC formulation additionally comprising the adjuvant Turbocharge® at 0.5% w/w.

As in Example 1, wheat plants were inoculated with the fungus *Septoria tritici*. Five days after inoculation the plants were sprayed with a diluted emulsion concentrate or suspension concentrate formulation of the fungicide isopyrazam at rates of 3, 10, 30 and 100 mg of the fungicide per liter of spray solution, using a laboratory track sprayer which delivered the spray at a rate of 200 liters per hectare. Spray tests were also carried out with diluted suspension concentrate additionally comprising each of the benzoate adjuvants described above. These adjuvants were added to the spray solution at a rate of 0.2% w/w, based on the quantity of spray liquor. The adjuvant oils were emulsified using a small amount of the surfactant Pluronic® PE 10500, which was present in the composition at a concentration of 0.02% v/v. The leaves of the plants were assessed visually 14 days after the spray application and the damage was expressed as the percentage of the leaf area infected. Each spray test was replicated three times across the four application rates and the modelled means of these results are shown in Table 3 below.

TABLE 3

Mean % infection of wheat plants with *S. tritici* treated with cyproconazole in the presence and absence of aromatic acid ester adjuvants. A standard Tukey HSD test was carried out to assess whether each result was statistically different from the other results and this is expressed as a letter: tests with the same letter are not statistically different ($p < 0.05$).

| Treatment | Mean % infection |
|---|---|
| Blank | 22.1 A |
| Standard epoxyconazole SC | 9.4 B |
| Standard epoxyconazole SC + tri-isodecyltrimellitate | 10 B |
| Stahndard epoxyconazole SC + Tri-n-hexyltrimellitate | 8.4 BC |
| Standard epoxyconazole SC + Turbocharge ® | 5.5 B |

As can be seen from Table 3 epoxyconazole compositions comprising the trimellitate compounds were as efficacious as the standard suspension concentrate formulation of cyproconazole in controlling *S. tritici* infection. Furthermore, inclusion of tri-n-hexyltrimellitate in an epoxyconazole composition resulted in a similar level of efficacy to that achieved when commercially available adjuvant Turbocharge was employed.

Example 3

Use of tri-n-hexyltrimellitate as an Adjuvant in Compositions of Nicosulfuron The efficacy of the aromatic acid ester Morflex ®560 (tri-n-hexyltrimellitate) as an adjuvant for the herbicide nicosulfruon was tested against four weed species in a glasshouse and compared to the well-know adjuvants, tris-2-ethylhexyl phosphate and acetyl tributyl citrate which were tested at concentrations of 0.2% w/w. The adjuvant oils were emulsified using a small amount of the surfactant Pluronic® PE 10500, which was present in the composition at a concentration of 0.02% v/v.

An agrochemical composition was prepared containing 0.2% v/v of the adjuvant in a track sprayer, and was applied at a volume of 200 liters per hectare. Nicosulfuron was applied at a rate of either 30 or 60 grams of pesticide per hectare. The weed species and their growth stage at spraying were *Abutilon theophrasti* (ABUTH; growth stage 13), *Chenopodium album* (CHEAL; growth stage 14), *Digitaria sanguinalis* (DIGSA; growth stage 13), and *Setaria viridis* (SETVI; growth stage 13).

Each spray test replicated three times. The efficacy of the herbicide was assessed visually and expressed as a percentage of the leaf area killed. Samples were assessed at time periods of 14 and 21 days following application. The results shown in Table 4 below are mean averages over the two rates of nicosulfuron, three replicates, two assessment timings and four species, and are compared to the efficacy of nicosulfuron in the absence of an adjuvant, and nicosulfuron in the presence of the commercially available adjuvants tris-2-ethylhexyl phosphate or acetyl tributyl citrate.

TABLE 4

Mean percentage kill results for nicolsulfuron in the presence and absence of tri-n-hexyltrimellitate, tris-2-ethylhexyl phosphate and acetyl tributyl citrate. A standard Tukey HSD test was carried out to assess whether each result was statistically different from the other results and this is expressed as a letter: tests with the same letter are not statistically different ($p < 0.05$).

| Treatment | Mean across species |
|---|---|
| Nicosulfuron + tris-2-ethylhexyl phosphate | 66.4 A |
| Nicosulfuron + tri-n-hexyltrimellitate | 60.7 A |
| Nicosulfuron + acetyl tributyl citrate | 58.8 A |
| Nicosulfuron | 42.5 B |

The results show that the inclusion of each of the known adjuvants and also of tri-n-hexyltrimellitate increases the efficacy of the herbicide nicosulfuron. Furthermore, it can be seen that tri-n-hexyltrimellitate is as effective an adjuvant as either tris-2-ethylhexylphosphate or acetyl tributyl citrate.

Example 4

Use of tri-n-hexyltrimellitate as an Adjuvant in Compositions of Fomesafen

The efficacy of the aromatic acid ester Morflex ®560 (tri-n-hexyltrimellitate) as an adjuvant for the herbicide fomesafen was tested against four weed species in a glasshouse and compared to the well-know adjuvants, acetyl tributyl citrate and Turbocharge® which were added at concentrations of 0.2 and 0.5% w/w respectively. The adjuvant oils were emulsified using a small amount of the surfactant Pluronic® PE 10500, which was present in the composition at a concentration of 0.02% v/v.

An agrochemical composition was prepared containing 0.2% v/v of the adjuvant in a track sprayer and was applied at a volume of 200 liters per hectare. Fomesafen was applied at either 60 or 120 grams of pesticide per hectare on each of the weed species. The weed species and their growth stage at spraying were *Chenopodium album* (CHEAL; growth stage 14), *Abutilon theophrasti* (ABUTH; growth stage 12), *Setaria viridis* (SETVI; growth stage 13), and *Xanthium strumarium* (XANST; growth stage 12).

Each spray test was replicated three times. The efficacy of the herbicide was assessed visually and expressed as a percentage of the leaf area killed. Samples were assessed at time periods of 7, 14 and 21 days following application. The results shown in Table 5 below are mean averages over the two rates of fomesafen, three replicates, four weed species and the three assessment timings, and are compared to the efficacy of fomesafen in the absence of an adjuvant, and fomesafen in the presence of the commercially available adjuvants acetyl tributyl citrate or Turbocharge®.

TABLE 5

Mean percentage kill results for fomesafen in the presence and absence of tri-n-hexyltrimellitate, acetyl tributyl citrate and Turbocharge ®. A standard Tukey HSD test was carried out to assess whether each result was statistically different from the other results and this is expressed as a letter: tests with the same letter are not statistically different ($p < 0.05$).

| Adjuvant | Mean across species |
|---|---|
| Fomesafen + tri-n-hexyltrimellitate | 45.0 A |
| Fomesafen + Turbocharge ® | 41.4 AB |
| Fomesafen + acetyl tributyl citrate | 37.5 BC |
| None | 22.5 D |

The results show that the inclusion of each of the known adjuvants and also of tri-n-hexyltrimellitate increases the efficacy of the herbicide fomesafen. Furthermore, it can be seen that tri-n-hexyltrimellitate is as effective an adjuvant as Turbocharge® and better than acetyl tributyl citrate.

Example 5

Use of tri-n-hexyltrimellitate as an Adjuvant in Compositions of Mesotrione

The efficacy of the aromatic ester tri-n-hexyltrimellitate (Morflex®560) was tested in a glasshouse against four weed species using the herbicide mesotrione. An agrochemical composition was prepared containing 0.2% v/v of the adjuvant in a track sprayer and was applied at a volume of 200 liters per hectare. The adjuvant oils were emulsified using a small amount of the surfactant Pluronic® PE 10500, which was present in the composition at a concentration of 0.02% v/v. Mesotrione was applied at either 45 or 90 grams of pesticide per hectare on weeds which had been grown to the 1.3 or 1.4 leaf stage. The weed species were *Polygonum convolvulus* (POLCO), *Brachiaria platyphylla* (BRAPL) *Digitaria sanguinalis* (DIGSA) and *Amaranthus tuberculatus* (AMATU).

Each spray test was replicated three times. The efficacy of the herbicide was assessed visually and expressed as a percentage of the leaf area killed. Samples were assessed at time periods of 7, 14 and 21 days following application. The results shown in Table 6 below are mean averages over the two rates of mesotrione, three relicates, four weed species and the three assessment timings and are compared to the efficacy of mesotrione in the absence of an adjuvant, and mesotrione in the presence of the commercially available adjuvants acetyl tributyl citrate or Tween®20 which were used at concentrations of 0.2 and 0.5% w/w respectively.

The results show that the inclusion of each of the known adjuvants and also of tri-n-hexyltrimellitate increases the efficacy of the herbicide mesotrione. Furthermore, it can be seen that tri-n-hexyltrimellitate is as effective an adjuvant as either acetyl tributyl citrate or Tween®20.

TABLE 6

Mean percentage kill results for mesotrione in the presence and absence of tri-n-hexyltrimellitate, acetyl tributyl citrate, or Tween ® 20. A standard Tukey HSD test was carried out to assess whether each result was statistically different from the other results and this is expressed as a letter: tests with the same letter are not statistically different (p < 0.05).

| Treatment | Mean across species |
| --- | --- |
| Mesotrione + tri-n-hexyltrimellitate | 51.0 A |
| Mesotrrione + Tween ® 20 | 50.8 A |
| Mesotrione + acetyl tributyl citrate | 48.0 A |
| Mesotrione | 34.0 B |

Example 6

Use of tri-n-hexyltrimellitate as an Adjuvant in Compositions of Pinoxaden

The efficacy of the aromatic ester tri-n-hexyltrimellitate (Morflex®560) was tested in a glasshouse against four weed species using the herbicide pinoxaden. An agrochemical composition was prepared containing 0.2% v/v of the adjuvant in a track sprayer and was applied at a volume of 200 liters per hectare. The adjuvant oils were emulsified using a small amount of the surfactant Pluronic® PE 10500, which was present in the composition at a concentration of 0.02% v/v. Pinoxaden was applied at either 7.5 or 15 grams of pesticide per hectare on each of the weed species. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 14).

Each spray test was replicated three times. The efficacy of the herbicide was assessed visually and expressed as a percentage of the leaf area killed. Samples were assessed at time periods of 14 and 21 days following application. The results shown in table 7 below are mean averages over the two rates of pinoxaden, three replicates, four weed species and the two assessment timings, and are compared to the efficacy of pinoxaden in the absence of adjuvant and pinoxaden in the presence of the known adjuvant acetyl tributyl citrate which was used at a concentration of 0.2% w/w.

TABLE 7

Mean percentage kill results for pinoxaden in the presence and absence of tri-n-hexyltrimellitate, or acetyl tributyl citrate. A standard Tukey HSD test was carried out to assess whether each result was statistically different from the other results and this is expressed as a letter: tests with the same letter are not statistically different (p < 0.05).

| Treatment | Mean across species |
| --- | --- |
| Pinoxaden + tri-n-hexyltrimellitate | 57.8 A |
| Pinoxaden + acetyl tributyl citrate | 41.0 B |
| Pinoxaden | 11.4 C |

The results show that the inclusion of the known adjuvant acetyl tributyl citrate and also of tri-n-hexyltrimellitate increases the efficacy of the herbicide pinoxaden. Furthermore, it can be seen that tri-n-hexyltrimellitate is more effective an adjuvant than acetyl tributyl citrate.

Example 7

Use of tri-n-hexyltrimellitate (Morflex®560) and tri-isodecylmellitate (Morflex®530) as Adjuvants for Nicosulfuron The efficacy of the aromatic esters tri-n-hexyltrimellitate (Morflex®560) and tri-isodecylmellitate (Morflex®530) as adjuvants for nicosulfuron were tested in a glasshouse against four weed species. An agrochemical composition was prepared containing 0.2% v/v of the adjuvant in a track sprayer, and was applied at a volume of 200 liters per hectare. The adjuvant oils were emulsified using a small amount of the surfactant Pluronic® PE 10500, which was present in the composition at a concentration of 0.02% v/v. Nicosulfuron was applied at a rate of either 30 or 60 grams per hectare. The weed species and their growth stage at spraying were *Abutilon theophrasti* (ABUTH; growth stage 13), *Chenopodium album* (CHEAL; growth stage 14), *Digitaria sanguinalis* (DIGSA; growth stage 13), and *Setaria viridis* (SETVI; growth stage 13).

Each spray test was replicated three times. The efficacy of the herbicide was assessed visually and expressed as a percentage of the leaf area killed. Samples were assessed at time periods of 14 and 21 days following application. The results shown in Table 8 below are mean averages over the two rates of nicosulfuron, three replicates, four weed species and the two assessment timings, and are compared to the efficacy of nicosulfuron in the absence of adjuvant and nicosulfuron in the presence of the known adjuvants methyl oleate or Atplus®411F. In this experiment Atplus®411F was added at the higher rate of 0.5% v/v. The other adjuvants were added at 0.2% v/v.

TABLE 8

Mean percentage kill results for nicosulfuron in the presence and absence of tri-n-hexyltrimellitate, tri-isodecylmellitate, methyl oleate or Atplus ® 411F. A standard Tukey HSD test was carried out to assess whether each result was statistically different from the other results and this is expressed as a letter: tests with the same letter are not statistically different ($p < 0.05$).

| Treatment | Mean across species |
| --- | --- |
| Nicosulfuron + Atplus ® 411F | 68.3 A |
| Nicosulfuron + tri n-hexyl trimellitate | 66.9 AB |
| Nicosulfuron + methyl oleate | 59.5 BC |
| Nicosulfuron + tri-isodecyltrimellitate | 54.6 CD |
| Nicosulfuron | 31.1 E |

The results show that the inclusion of the known adjuvants Atplus®411F and methyl oleate, and also of tri-n-hexyltrimellitate or isotridecylmellitate increases the efficacy of the herbicide nicosulfuron. Furthermore, it can be seen that tri-n-hexyltrimellitate is more effective an adjuvant than methyl oleate and as effective an adjuvant as Atplus®411F.

Example 8

Use of tri-n-hexyltrimellitate (Morflex®560) and tri-isodecylmellitate (Morflex®530) as Adjuvants for Pinoxaden The efficacy of the aromatic esters tri-n-hexyltrimellitate (Morflex®560) and tri-isodecylmellitate (Morflex®530) as adjuvants for pinoxaden were tested in a glasshouse against four weed species. An agrochemical composition was prepared containing 0.2% v/v of the adjuvant in a track sprayer and was applied at a volume of 200 liters per hectare. Pinoxaden was applied at either 7.5 or 15 grams per hectare on each of the weed species. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 14).

Each spray test was replicated three times. The efficacy of the herbicide was assessed visually and expressed as a percentage of the leaf area killed. Samples were assessed at time periods of 7 and 14 days following application. The results shown in Table 9 below are mean averages over the two rates of pinoxaden, three replicates, four weed species and the two assessment timings. The results were compared to the efficacy of pinoxaden in the absence of an adjuvant and pinoxaden in the presence of either tri-2-ethylhexyl phosphate (applied at 0.5% v/v) or methyl oleate (applied at 0.2% v/v).

TABLE 9

Mean percentage kill results for pinoxaden in the presence and absence of tri-n-hexyltrimellitate, tri-isodecylmellitate, tri-2-ethylhexyl phosphate or methyl oleate. A standard Tukey HSD test was carried out to assess whether each result was statistically different from the other results and this is expressed as a letter: tests with the same letter are not statistically different ($p < 0.05$).

| Adjuvant | Mean across species |
| --- | --- |
| Pinoxaden + tri-2-ethylhexyl phosphate | 69.5 A |
| Pinoxaden + tri n-hexyl trimellitate | 57.1 BC |
| Pinoxaden + methyl oleate | 52.3 BC |
| Pinoxaden + tri-isodecyltrimellitate | 45.5 C |
| Pinoxaden | 2.3 D |

The results show that the inclusion of the known adjuvants methyl oleate and tri-2-ethylhexyl phosphate increases the efficacy of the herbicide pinoxaden. Inclusion of the aromatic esters tri-n-hexyltrimellitate and tri-isodecylmellitate also increases the efficacy of pinoxaden. It can thus be seen that both trimellitate derivatives are effective adjuvants.

Example 9

Use of tri-n-hexyltrimellitate as an Adjuvant in Agrochemical Compositions Containing Abamectin The efficacy of tri-n-hexyltrimellitate (Morflex® 560) as an adjuvant in compositions containing abamectin was tested and compared to the efficacy of abamectin compositions which lack this type of adjuvant. The Morflex 560 was present at 0.1% v/v in the abamectin compositions. The surfactants polyoxyethylene sorbitan monooleate and an ethoxylated castor oil were also present in all the abamectin compositions tested. Two week old French bean (*Phaseolus vulgaris*) plants were infested with a mixed population of two spotted spider mite *Tetranychus urticae*. One day after infestation the plants were treated with the test compositions, with a track sprayer from the top with a rate of 200 liters per hectare. Plants were incubated in the greenhouse for 10 days and the evaluation was done on mortality against Larva and Adults, just on the lower side (untreated) of the leaves. Each experiment was replicated twice and the results were averaged. The mortality against Larva and Adults was then averaged. In the control experiment the beans were sprayed with water and no mortality was observed. The beans were also sprayed with a composition without abamectin present, containing 0.1% v/v Morflex® 560 and no mortality was observed.

TABLE 10

% Mortality of *Tetranychus urticae* treated with abamectin in the presence and absence of tri-n-hexyltrimellitate (Morflex ® 560).

| | % mortality of *Tetranychus urticae* at different abamectin concentrations (ppm) | | | | | | | | |
| --- | --- | --- | --- | --- | --- | --- | --- | --- | --- |
| Treatment | 3 ppm | 1.5 ppm | 0.8 ppm | 0.4 ppm | 0.2 ppm | 0.1 ppm | 0.05 ppm | 0.025 ppm | 0.0125 ppm |
| Abamectin | 95 | 70 | 27 | 0 | 0 | | | | |
| Abamectin + Morflex ® 560 | | | | | | 100 | 97 | 70 | 67 | 60 |

As can be seen from Table 10, the inclusion of tri-n-hexyltrimellitate (Morflex®560) as an adjuvant for abamectin provided effective control of *Tetranychus urticae* at much lower concentrations of abamectin than are required in the absence of adjuvant.

The invention claimed is:

1. A ready-to-use agrochemical composition suitable for spray application comprising:
   i. an active ingredient
   ii. a surfactant
   iii. an aromatic ester of formula (I)

$$\text{(benzene ring)}-[R^1]_n \quad (I)$$

wherein
$R^1$ is $COOR^2$
n is an integer selected from 3, 4, 5 and 6; and
each $R^2$ is independently selected from the group consisting of $C_4$-$C_{20}$ alkyl, $C_4$-$C_{22}$ alkenyl, $C_4$-$C_{22}$ alkyldienyl and $C_6$-$C_{22}$ alkyltrienyl in an amount of about 0.05% to about 1% w/w based on the total composition.

2. The agrochemical composition according to claim 1, wherein n is 3.

3. The agrochemical composition according to claim 1, wherein each $R^2$ is independently $C_6$-$C_{20}$ alkyl.

4. The agrochemical composition according to claim 3, wherein each $R^2$ is independently $C_6$-$C_{13}$ alkyl.

5. The agrochemical composition according to claim 1, wherein each $R^2$ is independently selected from the group consisting of a $C_6$ alkyl group, a $C_8$ alkyl group and a $C_{10}$ alkyl group.

6. The agrochemical composition according to claim 1, wherein each $R^2$ is the same.

7. The agrochemical composition according to claim 1, wherein the active ingredient is present at a concentration in the range from about 0.001% to about 90% w/w.

8. The agrochemical composition according to claim 1, wherein the active ingredient is selected from the group consisting of: bicyclopyrone, mesotrione, fomesafen, tralkoxydim, napropamide, amitraz, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin, prothioconazole, thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin, halfenprox, paclobutrazole, 1-methylcyclopropene, benoxacor, cloquintocet-mexyl, cyometrinil, dichlormid, fenchlorazole-ethyl, fenclorim, flurazole, fluxofenim, mefenpyr-diethyl, MG-191, naphthalic anhydride and oxabetrinil.

9. The agrochemical composition according to claim 1, wherein the composition is formulated as, or comprised by a microcapsule.

10. The agrochemical composition according to claim 1, comprising at least one additional component selected from the group consisting of agrochemicals, adjuvants, surfactants, emulsifiers and solvents.

11. A method of controlling a pest, comprising applying a composition as defined in claim 1 to said pest or the locus of said pest.

12. A method of making an agrochemical composition as claimed in claim 1, comprising combining the agrochemically active ingredient, surfactant and aromatic ester of formula (I) of claim 1.

* * * * *